United States Patent [19]

Sato et al.

[11] Patent Number: 4,654,457
[45] Date of Patent: Mar. 31, 1987

[54] METHOD FOR SELECTIVE DEALKYLATION OF 1,4-DIALKYLBENZENE

[75] Inventors: Hiroshi Sato; Norio Ishii; Kenichi Hirose, all of Osaka, Japan

[73] Assignee: Sumitomo Chemical Company, Limited, Osaka, Japan

[21] Appl. No.: 788,290

[22] Filed: Oct. 17, 1985

[51] Int. Cl.⁴ .............................................. C07C 4/12
[52] U.S. Cl. ...................................... 585/486; 585/489
[58] Field of Search ............................... 585/486, 489

[56] References Cited

U.S. PATENT DOCUMENTS 4,181,811  1/1980  Young ................................... 585/486
4,205,189  5/1980  Young et al. ......................... 585/481
4,499,321  2/1985  Sato et al. ............................ 585/486

FOREIGN PATENT DOCUMENTS

0127410A2  12/1984  European Pat. Off. .
0032621A1   7/1981  European Pat. Off. .
0109962A1   6/1984  European Pat. Off. .

Primary Examiner—Curtis R. Davis
Attorney, Agent, or Firm—Sughrue, Mion, Zinn, Macpeak & Seas

[57] ABSTRACT

A method for selectively dealkylating a 1,4-dialkylbenzene in a dialkylbenzene mixture is disclosed, comprising contacting the mixture with a zeolite catalyst which is prepared by the steps of: (1) hydrothermally synthesizing a zeolite from a system in which an alkali metal cation and an organic cation or its precursor coexist and then calcining the zeolite; and (2) modifying the zeolite with a metal or metalloid oxide. This method permits selective dealkylation of a 1,4-dialkylbenzene while maintaining the yield and purity of olefins formed during the dealkylation at high levels.

10 Claims, No Drawings

METHOD FOR SELECTIVE DEALKYLATION OF 1,4-DIALKYLBENZENE

FIELD OF THE INVENTION

The present invention relates to a method for shape-selectively dealkylating a 1,4-dialkylbenzene in a dialkylbenzene mixture using a specified zeolite catalyst, to thereby remove the 1,4-dialkylbenzene from the mixture or reducing its concentration of the mixture. More particularly, the present invention is intended to inhibit the side reaction (e.g., oligomerization, cracking, etc.) of an olefin produced by the above described dealkylation and to keep the percent recovery and purity of the liberated olefin at a high level, to thereby facilitate the reuse of the olefin and improve the economy of the dealkylation.

BACKGROUND OF THE INVENTION

Generally, dialkylbenzenes obtained by the dealkylation of benzenes are a mixture of 1,2-, 1,3- and 1,4-isomers, but a difference in boiling point between these isomers is so small that, in many cases, even rectifying columns having many plates are insufficient to separate these isomers from one another by distillation. Next, one specific example will be given. Cymene isomers obtained by the alkylation of toluene with propylene have the following boiling points: o-Isomer, 178.3° C.; m-isomer, 175.1° C.; and p-isomer, 177.1° C. A difference in boiling point between m- and p-cymenes, which comes into special question in the cresol manufacturing process, is only 2° C., so that separation of the both by rectification is extremely difficult. In the cresol manufacturing process now in use, therefore, the following procedure is employed: The mixed cymene, without being separated into the isomers, is oxidized as such into a mixed cresol (in this oxidation, the oxidation rate of o-cymene is very slow as compared with that of m- and p-cymenes so that the mixed cresol obtained consists mainly of m-cresol and p-cresol in general), and thereafter, separation of the cresol isomers is carried out.

As one method to separate the cresol isomers from one another, there is a method in which the cresol mixture is alkylated with isobutylene into a mixture of tert-butyl cresol isomers, the isomers are separated from one another by rectification taking advantage of a large difference in boiling point between them, and then the tertiary butyl group is eliminated to obtain high-purity m- and p-cresols.

As another method to separate the cresol isomers from one another, there is a method in which a mixture of cresol urea isomeric clathrate compounds is separated into the isomers by recrystallization taking advantage of a difference in crstallizability between them, and the separated compounds are decomposed to obtain high-purity m- and p-cresols.

The foregoing both methods are a separation method now in use in industry, but their process is so complicated that a furthermore improvement is desired.

Another specific example will be given below. Diisopropylbenzene obtained by the alkylation of benzene, which is a starting material for 1,3-dihydroxybenzene (resorcinol) and 1,4-dihydroxybenzene (hydroquinone), comprises the isomers having the following boiling points: o-Isomer, 200° C.; m-isomer, 203.2° C.; and p-isomer, 210.3° C. A difference in boiling point between m- and p-diisopropylbenzenes, which comes into special question in the resorcinol and hydroquinone manufacturing process, is 7° C., so that separation of the both by rectification is possible. This method, however, requires rectifying columns having a fairly large number of plates so that it may not always be said to be a separation method of good efficiency.

Instead of these conventional separation methods, there are proposed ones based on a new idea which are intended to selectively dealkylate only the 1,4-dialkyl isomer in the dialkylbenzene, to thereby recover the 1,3-dialkyl isomer (in some cases, 1,2- plus 1,3-dialkyl isomers) as unreacted (Japanese Patent Application (OPI) Nos. 83716/1980 and 83721/1980). (The term "OPI" as used herein refers to a "published unexamined Japanese patent application", hereinafter the same.) This method uses a ZSM type zeolite as a catalyst, and particularly, a ZSM type zeolite catalyst modified with oxides such as MgO, $P_2O_5$, etc. will dealkylate only the 1,4-dialkyl isomer with a very high selectivity, so that this method is a markedly epoch-making technique.

From the practical point of view, however, this method also has one large defect that, when the alkyl group to be dealkylated has not less than three carbon atoms, olefins obtained by the dealkylation are low in purity and percent recovery. For example, Example 10 of Japanese Patent Application (OPI) No. 83716/1980 discloses that m-cymene is obtained in a high purity (96.6%) by dealkylating a mixed cymene (o:m:p=2.16:66.16:31.67) using a steam-treated H-ZSM-5, but the content of recovered propylene in the volatile gas obtained at that time is about 60%. Similarly, Example 11 of Japanese Patent Application (OPI) No. 83721/1980 discloses that a high-purity m-cymene is obtained by dealkylating a mixed cymene using a similar catalyst, but the content of propylene recovered at that time is 43%. In the above two cases, the volatile gas contains $C_2$–$C_5$ hydrocarbons in addition to propylene. When an industrial process is taken into account, olefins produced by dealkylation (propylene in the case of dealkylation of cymene) need to be reused by recycling to the alkylation zone, otherwise the material cost becomes too high to establish a practical industrial process. When the olefin purity is however low, the olefin is difficult to reuse as it is, and therefore separate olefin-purification equipments become necessary, which is a defect of this method.

On the other hand, Japanese Patent Application (OPI) No. 103119/1981 discloses that when the reaction is carried out in the presence of an H-ZSM-5 catalyst while feeding a mixed cymene and aniline or ammonia, the dealkylation proceeds with a high para-selectivity, whereby propylene is recovered in a high purity as 94%. Through this method is an excellent technique, it has the following defects: Namely, when an actual embodiment to be applied industrially is taken into account, while the recovered propylene is recycled into the alkylation region, if a base such as aniline or ammonia is entrained, the dealkylating catalyst becomes deactivated. Thus, it is necessary to separate aniline or ammonia and to purify propylene, which results in rendering the process not ecomonical.

SUMMARY OF THE INVENTION

An object of the present invention is to provide a method for selectively dealkylating a 1,4-dialkylbenzene.

Another object of the present invention is to improve the purity of olefins recovered after the dealkylation.

A further object of the present invention is to obtain a 1,3-dialkylbenzene (m-isomer) in a state that the purity thereof is high or the proportion thereof is dominant, from a mixed dialkylbenzene.

Still a further object of the present invention is to obtain dialkylbenzenes such as m-cresol or resorcinol in a state that the purity thereof is high or the proportion thereof is dominant.

DETAILED DESCRIPTION OF THE INVENTION

First, the present inventors began with making a follow-up test on the prior arts, i.e., aforementioned Japanese Patent Application (OPI) Nos. 83716/1980 and 83721/1980.

From the test results shown in the comparative experiments, it was confirmed that, when the mixed cymene was dealkylated using as a catalyst ZSM type zeolite (e.g., ZSM-5) modified with the oxide of a metal or metalloid (e.g., MgO), only p-cymene was dealkylated with a high selectivity, but at the same time, it became also clear that the purity and percent recovery of the recovered propylene were extremely low. The volatile gas obtained at that time contains many kinds of $C_2$–$C_6$ olefins and paraffins in addition to propylene, from which it is supposed that the liberated isopropyl group was subjected to complicated side reactions such as oligomerization, cracking, hydrogenation, etc. Also, the total carbon content of the $C_2$–$C_6$ volatile gases is lower than that of the liberated isopropyl groups, from which it is supposed that some parts of the volatile gases were changed to heavy components having more than six carbon atoms.

In order to increase the yield and purity of recovered olefins, the present inventors have made further investigations. As a result, the following fact has been discovered: If a catalyst prepared by ion-exchanging an H-type crystalline zeolite with lithium ions is used, other side reactions can be prevented while maintaining dealkylation activity and, in this case, if a zeolite modified with metal or metalloid oxides is used, only a 1,4-isomer of dialkylbenzene can be selectively dealkylated. Based on this discovery, a patent application has been made (Japanese Patent Application No. 89570/1983 (corresponding to U.S. Pat. No. 4,499,321)).

As a result of further investigations, the present inventors have discovered that in the case of a crystalline zeolite prepared by a hydrothermal reaction under specific conditions, when it is modified with metal or metalloid oxides without any ion exchange treatment as in the above method, only the 1,4-isomer of dialkylbenzene can be selectively dealkylated while preventing side reactions using the modified zeolite as a catalyst. Based on this discovery, the present invention has been accomplished.

Accordingly, the present invention relates to a method for selectively dealkylating a 1,4-dialkylbenzene in a dialkylbenzene mixture by the use of a crystalline zeolite having a silica/alumina ratio of at least 12/1 and a constrained index of 1 to 12 as a catalyst, wherein the zeolite is prepared by synthesizing from a mixture of an alkali metal cation and an organic cation or an organic cation precursor by a hydrothermal reaction and then calcining in the state that the zeolite contains both the cations, and the zeolite is modified with a metal or metalloid oxide.

In the present invention, the dialkylbenzene to which the gist of the present invention can apply particularly advantageously is compounds containing a secondary and/or tertiary alkyl group having 3 to 12 carbon atoms. Specific examples of the 1,4-dialkylbenzene include, for example, 1-isopropyl-4-methylbenzene, 1,4-diisopropylbenzene, 1-sec-butyl-4-methylbenzene, 1-tert-butyl-4-methylbenzene, and the like. The effect of the present invention consists in two points: The first point is that the 1,4-dialkylbenzene alone contained in the dialkylbenzene mixture can selectively be dealkylated; and the second point is that the formed olefin (e.g., propylene for 1-isopropyl-4-methylbenzene or isobutylene for 1-tert-butyl-4-methylbenzene) can be recovered in a high yield and high purity.

Consequently, by incorporating the method of the present invention after the usual alkylation, the m-dialkyl isomer (or m- and o-dialkyl isomers) can be obtained in a high purity, and besides benzenes and olefins produced by dealkylation can be recycled as such to the alkylation step. This method, therefore, becomes a very rational process. Depending upon the object, this method may be used in such a manner as to regulate the isomer distribution only by limiting the percent dealkylation of the p-isomer to a specified range.

Next, the method of the present invention will be illustrated specifically. The crystalline aluminosilicate zeolite catalyst used in the present invention (hereinafter referred to as zeolite catalyst) is a novel zeolite having characteristics that the silica/alumina molar ration is 12/1 or more and besides the constrained index (described later) is 1 to 12, and its typical example is those (pentacyl type zeolites) which were developed by Mobile Oil Co. in relatively recent years and are generically called "ZSM type zeolite".

The characteristic of ZSM type zeolite is a high silica/alumina molar ratio, and this molar ratio can be measured by the common analytical methods such as atomic absorption method. This molar ratio expresses a value as near to the molar ratio in the skeleton of zeolite crystals as possible, with the exception of aluminum contained in the binder, cations in the channel and other forms. An effective zeolite is one having a silica/alumina molar ratio of at least 12/1, but in some cases, zeolite having silica/alumina molar ratios as very high as, for example, 500/1 is also effective.

The constrained index used in the present invention is defined by the following equation:

$$\text{Constrained index} = \frac{\log_{10}(\text{content of remaining hexane})}{\log_{10}(\text{content of remaining 3-methylpentane})}$$

This index was originally thought out by the research workers of Mobile Oil Co., and it means a degree to which the channel of the zeolite crystal controls the access to itself of molecules having a section larger than that of n-paraffin. The specific measurement method is described in Japanese Patent Application (OPI) No. 133223/1981.

The value of this constrained index approaches the ratio of cracking rates of the both hydrocarbons.

A preferred zeolite of the present invention is one having a constrained index of 1 to 12. The constrained index of some typical zeolites is shown below:

| | Constrained Index | Reference |
|---|---|---|
| ZSM-5 | 8.3 | Japanese Patent Publication No. 10064/1971 |
| ZSM-11 | 8.7 | Japanese Patent Publication No. 23280/1978 |
| ZSM-12 | 2 | Japanese Patent Publication No. 16079/1977 |
| ZSM-23 | 9.1 | Japanese Patent Application (OPI) No. 149900/1976 |
| ZSM-35 | 4.5 | Japanese Patent Application (OPI) No. 144500/1978 |
| ZSM-38 | 2 | U.S. Pat. No. 4,046,859 |
| ZSM-48 | 3.4 | Japanese Patent Application (OPI) No. 133223/1981 |

The value of the constrained index is the important critical definition of a useful zeolite in the present invention. Since, however, some latitude is allowed in the measurement method described above, the value sometimes varies with the measurement condition.

Consequently, the value of the constrained index is a mean value of those obtained under some different measurement conditions.

By referring to the above references disclosing the examples of the ZSM type zeolite that can be used in the present invention, the ZSM type zeolites can be identified by their X-ray diffraction patterns.

The first essential requirement for the method of the present invention is that the effect of the present invention can be obtained only when the above crystalline zeolite is hydrothermally synthesized under specific conditions. That is, in general, the ZSM type zeolite can be synthesized by the following three methods, but only the zeolite prepared by the first method can be used in the present invention.

METHOD OF SYNTHESIS OF ZSM TYPE ZEOLITE

1. Method of hydrothermally synthesizing from a system containing both an alkali metal cation and an organic cation or its precursor (for example, Japanese Patent Publication Nos. 10064/1971, 23280/1978, and 16079/1977, British Patent No. 1,402,981, and Japanese Patent Application (OPI) No. 73618/1981).

2. Method of hydrothermally synthesizing from a system containing an alkali metal cation as a single cation source (for example, Japanese Patent Publication No. 49851/1981 and Japanese Patent Application (OPI) Nos. 45111/1983 and 88119/1983).

3. Method of hydrothermally synthesizing from a system containing an organic cation or its precursor as a single cation source (for example, Japanese Patent Application (OPI) No. 125299/1978).

As the alkali metal cation to be used in the hydrothermal synthesis of the zeolite in the method of the present invention, lithium, sodium, potassium, rubidium and cesium can be used alone or in combination. Particularly preferred is a sodium cation. As the organic cation or its precursor that is used in the form of coexistence with the alkali metal cation, nitrogen-containing organic compounds such as tetraalkyl ammonium ions, linear or cyclic amines, polyalkylenepolyamines, and aminoalcohols can be used. Representative examples of the nitrogen-containing organic compounds are tetra-n-propylammonium bromide, tetra-n-propylammonium hydroxide, tetra-n-butylammonium bromide, tetraethylammonium bromide, trimethyl-2-hydroxyethylammonium chloride, tri-n-propylmethylammonium chloride, tri-n-propylamine, triethylamine, pyrrolidine, piperadine, ethylenediamine, and hexamethylenediamine. Of these compounds, a tetra-n-propylammonium cation is particularly preferred.

In the method of the present invention, the zeolite capable of becoming a base providing the desired catalytic performance can be obtained by calcining the zeolite synthesized hydrothermally in the condition that it contains both the alkali metal cation and organic cation. If, on the other hand, the zeolite is calcined in the condition that it contains only either the alkali metal cation or the organic cation, the desired catalytic performance cannot be obtained.

Calcination is carried out at a temperature of 350° to 600° C. in a stream of air or nitrogen for several hours.

The second essential requirement for the method of the present invention is that the above zeolite is modified with metal or metalloid oxides.

In this modification method, the ZSM type zeolite is treated either by the dipping method in which the zeolite is dipped in a solution containing a metal or metalloid compound and the solution is concentrated (in some cases, a filtration process is included) or by the kneading method in which the zeolite is kneaded with the metal or metalloid compound in a dry or wet condition and, thereafter, calcined at a temperature of 400° to 600° C. in a stream of air whereupon the ZSM type zeolite is modified in the condition of the metal or metalloid oxide. In general, this modification method is commonly used as a technique to poison the acid sites of the surface outside its channels and to exhibit the so-called para-selectivity. In the method of the present invention, even if only the first essential requirement is satisfied, the purity of olefin is maintained at a high level only insufficiently. It is only when the second essential requirement of modification with the oxide is also satisfied that the effect of the present invention that a high purity olefin can be recovered can be obtained. As in the conventional methods, the para-selectivity in the dealkylation reaction can be obtained by modification with the oxide in the method of the present invention. But, it is a novel discovery that when the modification with the oxide is applied in combination with the ZSM type zeolite obtained under the specific conditions as defined in the first essential requirement, the catalyst performance as desired in the present invention can be obtained.

The metal or metalloid compound for modifying the ZSM type zeolite is a compound of at least one element selected from the group consisting of the lanthanum elements (e.g., La, Ce, and Nd), the Group IIa elements (Ba, Mg, and Sr), the Group IIb elements (e.g., Zn and Cd), the Group IIIa elements (e.g., Ga and In), the Group IVa elements (e.g., Ge, Sn, and Pb), the Group Va elements (e.g., P), the Group VIa elements (e.g., Te), the Group VIb elements (e.g., Cr, Mo, and W), and the Group VIIb elements (e.g., Mn and Re).

This metal compound or metalloid compound is mixed with the ZSM type zeolite in the form of a solution, and through the steps of concentration and calcination, it finally modifies the ZSM type zeolite catalyst in the form of, substantially, a metal oxide or metalloid oxide. Examples of a suitable solvent used in this case include for example water, aromatic or aliphatic hydrocarbons, alcohols, organic acids (e.g., formic acid, acetic acid, and propionic acid) and inorganic acids (e.g., hydrochloric acid, nitric acid, and sulfuric acid). Alternatively, halogenated hydrocarbons, ketones, ethers, etc. also are useful. Of these solvents, water is used most popularly. The ZSM type zeolite is impregnated with this solution, and after concentration, it is dried, but in some cases, it is filtered after impregnation and dried. Drying is carried out at a temperature of generally 80° C. to 150° C. Calcination after drying is carried out at a temperature of 300° C. or higher, preferably 400° to 550° C. for several hours in an air stream. The amount of the metal oxide or metalloid oxide modifying the ZSM type zeolite after calcination is selected from a range of 1 wt% to 50 wt%.

The dealkylation reaction in the method of the present invention will hereinafter be explained.

The dealkylation is mainly carried out by the gas-phase catalytic reaction.

The catalytic system of the present invention may be used alone but it is usually put into practical uses after diluting with a binder such as alumina and then press molding.

In this reaction, inert gases such as nitrogen, helium, argon, etc. may be used as a diluent. The use of the diluent may be employed for the purpose of positively aiming to control the occurrence of side reactions by the action of the dilution of the substrate, to thereby keep the purity of the recovered olefin high, if any. From an industrial standpoint, however, the above process is not always an economical process because the diluent is necessary to separate from light olefins, formed, thereby increasing a step of separation of the diluent from the light olefins. If possible, it is preferred that the reaction be carried out without use of the diluent. In this respect, the catalytic system of the present invention sufficiently satisfies the above requirement.

The reaction temperature cannot be determined simply because it is affected by the kind of alkyl groups to be dealkylated, but generally it is selected from a range of 250° to 600° C. The alkyl group which is an object of dealkylation of the present invention is a secondary and/or tertiary alkyl group having 3 to 12 carbon atoms. Generally, however, the progress of the dealkylation becomes easy as an increase in the number of carbon atoms of the alkyl group, or it is easier in tertiary alkyl groups than in secondary ones. The reaction temperature, therefore, shifts to a low temperature side.

One characteristic of the present catalytic system is that, if the dealkylation is carried out at high temperatures in order to raise its conversion, selectivity to the dealkylation of the 1,4-isomer is kept high (in other words, both the 1,2- and 1,3-isomers are left completely or nearly unreacted) and besides both the purity and percent recovery of the recovered olefin are also kept high.

The contact time is selected from a range of 0.1 to 60 seconds, preferably 1 to 30 seconds.

Another characteristic of the present catalytic system is that, if the dealkylation is carried out for a long contact time in order to raise its conversion, selectivity to the dealkylation of the 1,4-isomer as well as the yield and purity of the recovered olefin are kept high.

A further characteristic of the present catalytic system is that, since the catalytic system has a long life, a reduction in the catalytic activity due to deposition of carbonaceous substances is very little even in the prolonged reaction.

The dealkylation of the present invention is carried out using a fixed-bed or fluidized-bed catalytic system according to a batchwise, semi-continuous or continuous process. In either case, for the regeneration of the catalyst, carbonaceous substances on the catalyst are burned out at a temperature of about 500° to about 550° C. using an inert gas containing a little oxygen (0.5 to 2.0%).

The present invention will be illustrated in more detail with reference to the following specific examples, but it is not to be interpreted as being limited thereto.

The reaction results in the examples were calculated by means of the following equations.

$$\text{Total conversion (\%)} = \left(1 - \frac{\text{unreacted dialkylbenzene (mole)}}{\text{starting dialkylbenzene (mole)}}\right) \times 100$$

$$\text{Conversion of p-isomer (\%)} = \left(1 - \frac{\text{unreacted p-dialkylbenzene (mole)}}{\text{starting p-dialkylbenzene (mole)}}\right) \times 100$$

$$\text{Yield of monoalkylbenzene (\%)} = \frac{\text{formed monoalkylbenzene (mole)}}{\text{starting dialkylbenzene (mole)}} \times 100$$

$$\text{Yield of olefin (\%) (1)} = \frac{\text{formed olefin (1) (mole)}}{\text{starting dialkylbenzene (mole)}} \times 100$$

(1) An objective main olefin formed by dealkylation (e.g., propylene for cymene and isobutylene for tert-butyltoluene).

$$\text{Percent recovery of m-isomer (\%)} = \frac{\text{unreacted m-dialkylbenzene (mole)}}{\text{starting m-dialkylbenzene (mole)}} \times 100$$

$$\text{Percent recovery of o-isomer (\%)} = \frac{\text{unreacted o-dialkylbenzene (mole)}}{\text{starting o-dialkylbenzene (mole)}} \times 100$$

$$\text{Percent recovery of aromatic substance (\%)} = \frac{\text{recovered alkylbenzenes (mole)}}{\text{starting dialkylbenzene (mole)}} \times 100$$

$$\text{Percent recovery of gas (\%)} = \frac{\text{recovered gas}^{(2)} \text{ (carbon, g-atom)}}{\text{liberated alkyl group (carbon, g-atom)}} \times 100$$

(2) Total $C_1$–$C_6$ volatile olefins and paraffins.

$$\text{Purity of olefin (\%)}^{(1)} = \frac{\text{formed olefin}^{(1)} \text{ (mole)}}{\text{recovered gas}^{(2)} \text{ (mole)}} \times 100$$

The analysis of the reaction products was carried out by gas chromatography.

EXAMPLE 1

(1) Preparation of Catalyst

A starting solution each having the following formulation was first prepared.

| Solution A | |
|---|---|
| Water | 162 g |
| $H_2SO_4$ | 16.7 g |
| $Al_2(SO_4)_3 \cdot 17H_2O$ | 2.92 g |
| $(n\text{-Pr})_4NBr$ | 20.3 g |

-continued

| Solution B | |
|---|---|
| Water | 119.7 g |
| Sodium silicate No. 3 | 186.3 g |
| Solution C | |
| Water | 281.7 g |
| NaCl | 70.9 g |

The solutions A and B were dropped to the solution C at the same time and then mixed. At this time, the mixture was vigorously stirred while maintaining the pH at 9 to 11 (for this pH adjustment, 6.0 g of a 48% aqueous NaOH solution). The pH when the mixing was completed was 9.55. The mixture was placed in a 1-liter SUS autoclave and then was subjected to a hydrothermal reaction while stirring at 160° C. for 20 hours (N=120 rpm). After being cooled, the reaction mixture was filtered and thoroughly washed with a large amount (up to 7 liters) of distilled water. In this manner, the washing/filtration cycle was repeated. The reaction product was dried at 120° C. for 15 hours and then calcined at 530° C. for 3 hours in an air stream to yield 48.6 g of white powdered crystals (yield=88.8%).

The X-ray diffraction analysis confirmed that the product was ZSM-5. The degree of crystallinity was 90.5%. The fluorescent X-ray analysis showed that the $SiO_2/Al_2O_3$ molar ratio was 88.6/1.

3.0 g of the ZSM-5 thus obtained was mixed with 4.0 g of magnesium acetate tetrahydrate, and the resulting mixture was well kneaded in an agate mortar. After press molding, the molding was ground to 24 to 48 mesh particles. These particles were placed in a quartz glass reaction tube and then calcined at 500° C. for 3 hours in an air stream. In this way, a 20 wt% MgO-supported ZSM-5 catalyst was obtained.

(2) Catalytic Activity Test by the Fixed-Bed Flow Reaction

Dealkylation of cymene using the ordinary atmospheric pressure fixed-bed flow reactor was carried out as follows.

A quartz glass tube tubular reactor having a length of 32 cm and an inside diameter of 1 cm was charged with 1 g of the 20 wt% MgO-ZSM-5 catalyst prepared in (1) above, which was then preheated at 400° C. for 1 hour in an $N_2$ stream. Thereafter, a mixed cymene (m:p:o=63.6:32.9:3.5) was fed to the reactor at a WHSV (weight hourly space velocity) of 2.7 hr$^{-1}$ and reacted. The temperature of the catalyst bed (reaction temperature) was 450° C. The reaction product was collected by trapping by ice-cooling, and the aromatic component was analyzed by gas chromatography. The volatile gas component was analyzed in situ by introducing the mixed reaction gas directly into a gas chromatographic column.

The results are shown in Table 2.

EXAMPLES 2 TO 7

(1) In Example 1-(1), the amount of aluminum sulfate was changed to prepare ZSM-5s having different $SiO_2/Al_2O_3$ molar ratios. During mixing the solutions A, B and C, the pH was maintained at 9 to 11, and the pH after completion of the mixing was adjusted to 9 to 10. For this pH adjustment, caustic soda was used. In some cases, the number of agitation of the autoclave during the synthesis of the ZSM-5 was changed.

Each ZSM-5 thus prepared was calcined after supporting magnesium acetate by the dry kneading method to thereby prepare a 20 wt% MgO-supported ZSM-5 catalyst.

The results of synthesis of ZSM-5 are shown in Table 1.

(2) Dealkylation of cymene was carried out in the same manner as in (2) of Example 1 wherein the 20 wt% MgO-supported ZSM-5 catalysts having varied $SiO_2/Al_2O_3$ molar ratios as prepared in (1) of Examples 2 to 7 were each used in the amount of 1 g.

The results are shown in Table 2.

TABLE 1

| Example No. | Number of Agitation of Autoclave, N (r.p.m.) | Amount (g) | Yield (%) | $SiO_2/Al_2O_3$ Molar Ratio | Crystal Form | Degree of Crystallinity (%) |
|---|---|---|---|---|---|---|
| 1 (1) | 120 | 48.6 | 88.8 | 88.6/1 | ZSM-5 | 90.5 |
| 2 (1) | 120 | 54.2 | 97.7 | 52.2/1 | " | 86.0 |
| 3 (1) | 350 | 47.3 | 85.3 | 60.2/1 | " | 83.3 |
| 4 (1) | 120 | 49.4 | 86.7 | 33.4/1 | " | 80.1 |
| 5 (1) | 120 | 52.4 | 84.3 | 15.2/1 | " | 48.9 |
| 6 (1) | 350 | 51.9 | 83.5 | 15.8/1 | " | 53.1 |
| 7 (1) | 500 | 54.5 | 87.7 | 15.1/1 | " | 47.9 |

EXAMPLE 8

A catalyst was prepared in the same manner as in Example 7-(1) except that the amount of MgO supported was changed to 50 wt%. Using this catalyst, dealkylation of cymene was carried out in the same manner as in Example 1-(2).

The results are shown in Table 3.

EXAMPLE 9

A catalyst was prepared in the same manner as in Example 7-(1) except that the supporting of magnesium acetate was conducted by the impregnation-concentration method in place of the dry kneading method. Using this catalyst, dealkylation of cymene was conducted in the same manner as in Example 1-(2).

The results are shown in Table 3.

TABLE 2

| Example No. | $SiO_2/Al_2O_3$ Molar Ratio | Number of Agitation of Autoclave (r.p.m.) | Conversion (%) | | Yield (%) | | Percent Recovery of m-Cymene (%) | Purity of Propylene (%) |
|---|---|---|---|---|---|---|---|---|
| | | | p-Cymene | Total Cymene | Toluene | Propylene | | |
| 1-(2) | 88.6 | 120 | 53.0 | 21.6 | 20.2 | 19.3 | 94.8 | 98.1 |
| 2-(2) | 52.2 | 120 | 95.0 | 39.7 | 37.7 | 26.3 | 89.4 | 86.0 |
| 3-(2) | 60.2 | 350 | 91.0 | 40.6 | 35.9 | 32.1 | 85.5 | 95.3 |
| 4-(2) | 33.4 | 120 | 98.0 | 49.9 | 42.8 | 23.7 | 74.7 | 67.7 |

TABLE 2-continued

| Example No. | SiO$_2$/Al$_2$O$_3$ Molar Ratio | Number of Agitation of Autoclave (r.p.m.) | Conversion (%) | | Yield (%) | | Percent Recovery of m-Cymene (%) | Purity of Propylene (%) |
|---|---|---|---|---|---|---|---|---|
| | | | p-Cymene | Total Cymene | Toluene | Propylene | | |
| 5-(2) | 15.2 | 120 | 82.6 | 35.0 | 32.0 | 29.4 | 90.1 | 96.6 |
| 6-(2) | 15.8 | 350 | 61.7 | 23.7 | 22.2 | 21.2 | 96.4 | 99.2 |
| 7-(2) | 15.2 | 500 | 87.2 | 38.1 | 35.2 | 32.2 | 87.4 | 96.3 |

TABLE 3

| Example No. | Method of Supporting of MgO | Amount of MgO supported (wt %) | Conversion (%) | | Yield (%) | | Percent Recovery of m-Cymene (%) | Purity of Propylene (%) |
|---|---|---|---|---|---|---|---|---|
| | | | p-Cymene | Total Cymene | Toluene | Propylene | | |
| 7-(2) | Dry Kneading | 20 | 87.2 | 38.1 | 35.2 | 32.2 | 87.4 | 96.3 |
| 8 | Dry Kneading | 50 | 64.3 | 24.5 | 22.3 | 21.9 | 96.5 | 99.3 |
| 9 | Impregnation-Concentration | 20 | 73.0 | 27.1 | 25.8 | 23.1 | 97.4 | 97.0 |

COMPARATIVE EXAMPLE 1

5 g of ZSM-5 having an SiO$_2$/Al$_2$O$_3$ molar ratio of 60.2/1 as synthesized in Example 3-(1) was subjected three times to an ion exchange treatment at 65° C. for 2 hours each using 20 g of a 5% aqueous ammonium chloride solution and further to an ion exchange treatment at 25° C. overnight using 20 g of a 5% aqueous ammonium chloride solution. Washing with 20 g of distilled water and filtration were repeated five times. Then the product was dried at 120° C. for 10 hours to yield NH$_4^+$-ZSM-5. This NH$_4^+$-ZSM-5 was calcined at 530° C. for 2 hours in an air stream to yield H$^+$-ZSM-5. 3.0 g of this H$^+$-ZSM-5 was mixed with 4.0 g of magnesium acetate tetrahydrate, and the resulting mixture was well kneaded in an agate mortar to achieve dry supporting. After press molding, the molding was ground to produce 24 to 48 mesh particles. These particles were packed in a quartz glass reaction tube and then calcined at 500° C. for 3 hours in an air stream. In this way, a 20 wt% MgO-H$^+$-ZSM-5 catalyst was obtained.

Using 1 g of the catalyst thus obtained, dealkylation of cymene was conducted in the same manner as in Example 1-(2). The results are shown in Table 4.

COMPARATIVE EXAMPLES 2 TO 8

The ZSM-5s having varied SiO$_2$/Al$_2$O$_3$ molar ratios as prepared in Examples 1-(1) to 7-(1) were used as such without supporting MgO. Dealkylation of cymene was conducted in the same manner as in Example 1-(2).

The results are shown in Table 5.

TABLE 4

Reaction Temperature = 350° C.

| No. | catalyst | Conversion (%) | | Yield (%) | | Percent Recovery of m-Cymene (%) | Purity of Propylene (%) |
|---|---|---|---|---|---|---|---|
| | | p-Cymene | Total Cymene | Toluene | Propylene | | |
| Comparative Example 1 | 20% MgO—H$^+$—ZSM-5 | 98.3 | 37.4 | 31.0 | 3.5 | 93.4 | 22.0 |

TABLE 5

Reaction Temperature = 350° C.

| No. | SiO$_2$/Al$_2$O$_3$ Molar Ratio | Number of Agitation of Autoclave | Conversion (%) | | Yield (%) | | Percent Recovery of m-Cymene (%) | Purity of Propylene (%) |
|---|---|---|---|---|---|---|---|---|
| | | | p-Cymene | Total Cymene | Toluene | Propylene | | |
| Comparative Example | | | | | | | | |
| 2 | 88.6/1 | 120 | 88.1 | 39.4 | 38.8 | 5.8 | 86.3 | 31.6 |
| 3 | 52.2/1 | 120 | 96.2 | 70.0 | 60.9 | 3.4 | 42.3 | 13.5 |
| 4 | 60.2/1 | 350 | 96.1 | 65.9 | 57.7 | 5.1 | 48.0 | 15.0 |
| 5 | 33.4/1 | 120 | 97.6 | 85.3 | 70.2 | 2.3 | 20.0 | 7.9 |
| 6 | 15.2/1 | 120 | 92.1 | 58.3 | 53.3 | 6.3 | 58.5 | 25.8 |
| 7 | 1.58/1 | 350 | 93.5 | 65.8 | 59.3 | 5.3 | 47.5 | 22.0 |
| 8 | 15.2/1 | 500 | 95.0 | 83.2 | 70.2 | 2.5 | 22.2 | 9.2 |

EXAMPLE 10

Using the MgO-ZSM-5 catalyst having an SiO$_2$/Al$_2$O$_3$ molar ratio of 52.2/1 as prepared in Example 2-(1), dealkylation of diisopropylbenzene (hereinafter abbreviated to "DCM") (m/p=65.5/34.5) as a feedstock was conducted in the same manner as in Example 1-(2).

The results are shown in Table 6.

TABLE 6

| Conversion (%) | | Percent Recovery | Yield* (%) | | | Purity of |
|---|---|---|---|---|---|---|
| p-DCM | Total DCM | of m-DCM | Cymene | Benzene | Propylene | Propylene (%) |
| 56.0 | 37.5 | 94.4 | 10.8 | 26.3 | 55.1 | 91.7 |

Note:
*Yield based on the DCM feedstock.

EXAMPLE 11

Using the MgO-ZSM-5 catalyst having an Si/Al=26.1/1 as prepared in Example 2-(1), dealkylation of tert-butyltoluene (m/p=65/35, hereinafter abbreviated to "TBT") as the feedstock was conducted in the same manner as in Example 1-(2).

The results are shown in Table 7.

TABLE 7

| Conversion (%) | | Percent Recovery of m-TBT (%) | Yield (%) | | Purity of Isobutylene (%) |
|---|---|---|---|---|---|
| p-TBT | Total TBT | | Toluene | Isobutylene | |
| 32.0 | 23.1 | 95.5 | 21.0 | 21.3 | 93.3 |

While the invention has been described in detail and with reference to specific embodiments thereof, it will be apparent to one skilled in the art that various changes and modifications can be made therein without departing from the spirit and scope thereof.

What is claimed is:

1. A method for selectively dealkylating a 1,4-dialkylbenzene in a dialkylbenzene mixture in the presence of as a catalyst a crystalline zeolite having an SiO$_2$/Al$_2$O$_3$ molar ratio of at least 12/1 and a constrained index of 1 to 12, wherein the zeolite is:
   (1) prepared by hydrothermally synthesizing a system containing both an alkali metal cation and an organic cation or its precursor and then calcining it in the condition that it contains both the cations; and
   (2) modified with a metal or metalloid oxide.

2. A method as claimed in claim 1, wherein the alkali metal is at least one metal selected from the group consisting of lithium, sodium, potassium, rubidium, and cesium.

3. A method as claimed in claim 1, wherein the organic cation or its precursor is an organic amine cation or its precursor selected from a tetraalkylammonium ion, a linear or cyclic amine, a polyalkylenepolyamine, and an aminoalcohol.

4. A method as claimed in claim 1, wherein the organic cation or its precursor is a tetra-n-propylammonium ion.

5. A method as claimed in claim 1, wherein the calcination is carried out at a temperature of 350° to 600° C. in a stream of air or nitrogen.

6. A method as claimed in claim 1, wherein the crystalline zeolite is ZSM-5, ZSM-11, ZSM-12, ZSM-23, ZSM-35, ZSM-38, or ZSM-48.

7. A method as claimed in claim 1, wherein the metal or metalloid oxide is an oxide of at least one element selected from the group consisting of La, Ce and Nd of the lanthanum group, Ba, Mg and Sr of the group IIa, Zn and Cd of the group IIb, Ga and In of the group IIIa, Ge, Sn and Pb of the group IVa, P of the group Va, Te of the group VIa, Cr, Mo and W of the group VIb, and Mn and Re of the group VIIb.

8. A method as claimed in claim 1, wherein the crystalline zeolite is ZSM-5, and the metal oxide which modifies the zeolite is magnesium oxide.

9. A method as claimed in claim 1, wherein at least one alkyl group of the 1,4-dialkylbenzene has 3 to 12 carbon atoms and is a secondary or tertiary alkyl group.

10. A method as claimed in claim 1, wherein the 1,4-dialkylbenzene is 1-isopropyl-4-methylbenzene, 1,4-diisopropylbenzene, 1-sec-butyl-4-methylbenzene, or 1-tert-butyl-4-methylbenzene.

* * * * *